United States Patent
Noordin et al.

(10) Patent No.: US 8,962,259 B2
(45) Date of Patent: Feb. 24, 2015

(54) RECOMBINANT ANTIGEN FOR DETECTION OF TOXOCARIASIS

(75) Inventors: Rahmah Binti Noordin, Penang (MY); Suharni Binti Mohamad, Penang (MY)

(73) Assignee: Universiti Sains Malaysia, Pedang (MY)

( * ) Notice: Subject to any disclaimer, the term of this patent is extended or adjusted under 35 U.S.C. 154(b) by 118 days.

(21) Appl. No.: 13/133,870

(22) PCT Filed: Feb. 27, 2009

(86) PCT No.: PCT/MY2009/000044
§ 371 (c)(1),
(2), (4) Date: Jun. 9, 2011

(87) PCT Pub. No.: WO2010/068084
PCT Pub. Date: Jun. 17, 2010

(65) Prior Publication Data
US 2012/0077187 A1    Mar. 29, 2012

(30) Foreign Application Priority Data
Dec. 12, 2008   (MY) .............................. PI 20085032

(51) Int. Cl.
| | | |
|---|---|---|
| *C12Q 1/68* | (2006.01) |
| *C12N 1/21* | (2006.01) |
| *C07K 14/435* | (2006.01) |
| *C12N 9/96* | (2006.01) |
| *G01N 33/53* | (2006.01) |

(52) U.S. Cl.
CPC .......... *C07K 14/4354* (2013.01); *C07K 2319/23* (2013.01); *G01N 33/5308* (2013.01); *G01N 2333/43526* (2013.01)
USPC ........ 435/7.1; 435/69.1; 435/188; 435/252.3; 435/320.1; 530/320

(58) Field of Classification Search
None
See application file for complete search history.

(56) References Cited

U.S. PATENT DOCUMENTS

| | | |
|---|---|---|
| 5,871,738 A | 2/1999 | Sharp et al. |
| 5,948,644 A | 9/1999 | Dopheide et al. |
| 6,103,484 A | 8/2000 | Carlow et al. |

OTHER PUBLICATIONS

Gems et al., "An Abundant, trans-spliced mRNA from Toxocara canis Infective Larvae Encodes a 26-kDa Protein with Homology to Phosphatidylethanolamine-binding Proteins," J. Biol. Chem. 1995, vol. 270, No. 31, pp. 18517-18522.
Norhaida et al., "rTES-30USM: cloning via assembly PCR, expression, and evaluation of usefulness in the detection of toxocariasis," Ann. Trop. Med. Parasitol. 2007, vol. 102, No. 1, pp. 1-10.
Terpe, "Overview of tag protein fusions: from molecular and biochemical fundamentals to commercial systems," Appl. Microbiol. Biotechnol. 2003, vol. 60, pp. 523-533.

*Primary Examiner* — Robert A Zeman
(74) *Attorney, Agent, or Firm* — Preston Smirman; Smirman IP Law, PLLC

(57) ABSTRACT

A vector comprising a polynucleotide sequence encoding a polypeptide having an amino acid sequence of SEQ ID NO: 2 for detecting antibody against *Toxocara* spp. in a biological sample.

3 Claims, 3 Drawing Sheets

SEQ ID NO: 1

Met Ser Pro Ile Leu Gly Tyr Trp Lys Ile Lys Gly Leu Val Gln Pro Thr Arg Leu Leu
Leu Glu Tyr Leu Glu Glu Lys Tyr Glu Glu His Leu Tyr Glu Arg Asp Glu Gly Asp Lys
Trp Arg Asn Lys Lys Phe Glu Leu Gly Leu Glu Phe Pro Asn Leu Pro Tyr Tyr Ile Asp
Gly Asp Val Lys Leu Thr Gln Ser Met Ala Ile Ile Arg Tyr Ile Ala Asp Lys His Asn Met
Leu Gly Gly Cys Pro Lys Glu Arg Ala Glu Ile Ser Met Leu Glu Gly Ala Val Leu Asp
Ile Arg Tyr Gly Val Ser Arg Ile Ala Tyr Ser Lys Asp Phe Glu Thr Leu Lys Val Asp Phe
Leu Ser Lys Leu Pro Glu Met Leu Lys Met Phe Glu Asp Arg Leu Cys His Lys Thr Tyr
Leu Asn Gly Asp His Val Thr His Pro Asp Phe Met Leu Tyr Asp Ala Leu Asp Val Val
Leu Tyr Met Asp Pro Met Cys Leu Asp Ala Phe Pro Lys Leu Val Cys Phe Lys Lys Arg
Ile Glu Ala Ile Pro Gln Ile Asp Lys Tyr Leu Lys Ser Ser Lys Tyr Ile Ala Trp Pro Leu
Gln Gly Trp Gln Ala Thr Phe Gly Gly Gly Asp His Pro Pro Lys Ser Asp Gly Ser Thr
Ser Gly Ser Gly His His His His His His Ser Ala Gly Leu Val Pro Arg Gly Ser Thr Ala
Ile Gly Met Lys Glu Thr Ala Ala Ala Lys Phe Glu Arg Gln His Met Asp Ser Pro Asp
Leu Gly Thr Gly Gly Gly Ser Gly Ile Glu Gly Arg Gly Ser Met Asp Ile Gly Asp Pro
Asn Ser Pro Phe Thr Met Ser Val Val His Lys Ala Cys Leu Ile Ala Leu Leu Phe Val
Ser Ser Gly Val Ala Gln Gln Cys Met Asp Ser Ala Ser Asp Cys Ala Ala Asn Ala Gly
Ser Cys Phe Thr Arg Pro Val Ser Gln Val Leu Gln Asn Arg Cys Gln Arg Thr Cys Asn
Thr Cys Asp Cys Arg Asp Glu Ala Asn Asn Cys Ala Ala Ser Ile Asn Leu Cys Gln Asn
Pro Thr Phe Glu Pro Leu Val Arg Asp Arg Cys Gln Lys Thr Cys Gly Leu Cys Ala Gly
Cys Gly Phe Ile Ser Ser Gly Ile Val Pro Leu Val Val Thr Ser Ala Pro Ser Arg Arg Val
Ser Val Thr Phe Ala Asn Asn Val Gln Val Asn Cys Gly Asn Thr Leu Thr Thr Ala Gln
Val Ala Asn Gln Pro Thr Val Thr Trp Glu Ala Gln Pro Asn Asp Arg Tyr Thr Leu Ile
Met Val Asp Pro Asp Phe Pro Ser Ala Ala Asn Gly Gln Gln Gly Gln Arg Leu His Trp
Trp Val Ile Asn Ile Pro Gly Asn Asn Ile Ala Gly Gly Thr Thr Leu Ala Ala Phe Gln Pro
Ser Thr Pro Ala Ala Asn Thr Gly Val His Arg Tyr Val Phe Leu Val Tyr Arg Gln Pro
Ala Ala Ile Asn Ser Pro Leu Leu Asn Asn Leu Val Val Gln Asp Ser Glu Arg Pro Gly
Phe Gly Thr Thr Ala Phe Ala Thr Gln Phe Asn Leu Gly Ser Pro Tyr Ala Gly Asn Phe
Tyr Arg Ser Gln Ala

Figure 1

SEQ ID NO: 2

Met Ser Val Val His Lys Ala Cys Leu Ile Ala Leu Leu Phe Val Ser Ser Gly Val Ala Gln Gln Cys Met Asp Ser Ala Ser Asp Cys Ala Ala Asn Ala Gly Ser Cys Phe Thr Arg Pro Val Ser Gln Val Leu Gln Asn Arg Cys Gln Arg Thr Cys Asn Thr Cys Asp Cys Arg Asp Glu Ala Asn Asn Cys Ala Ala Ser Ile Asn Leu Cys Gln Asn Pro Thr Phe Glu Pro Leu Val Arg Asp Arg Cys Gln Lys Thr Cys Gly Leu Cys Ala Gly Cys Gly Phe Ile Ser Ser Gly Ile Val Pro Leu Val Val Thr Ser Ala Pro Ser Arg Arg Val Ser Val Thr Phe Ala Asn Asn Val Gln Val Asn Cys Gly Asn Thr Leu Thr Thr Ala Gln Val Ala Asn Gln Pro Thr Val Thr Trp Glu Ala Gln Pro Asn Asp Arg Tyr Thr Leu Ile Met Val Asp Pro Asp Phe Pro Ser Ala Ala Asn Gly Gln Gln Gly Gln Arg Leu His Trp Trp Val Ile Asn Ile Pro Gly Asn Asn Ile Ala Gly Gly Thr Thr Leu Ala Ala Phe Gln Pro Ser Thr Pro Ala Ala Asn Thr Gly Val His Arg Tyr Val Phe Leu Val Tyr Arg Gln Pro Ala Ala Ile Asn Ser Pro Leu Leu Asn Asn Leu Val Val Gln Asp Ser Glu Arg Pro Gly Phe Gly Thr Thr Ala Phe Ala Thr Gln Phe Asn Leu Gly Ser Pro Tyr Ala Gly Asn Phe Tyr Arg Ser Gln Ala

Figure 2

SEQ ID NO: 3

CACCATGTCAGTTGTACACAAAGCTTGC

SEQ ID NO: 4

TTAGGCCTGCGATCGATAGA

SEQ ID NO: 5

CAG GAA ACA GCT ATG AC

Figure 3

RECOMBINANT ANTIGEN FOR DETECTION OF TOXOCARIASIS

CROSS-REFERENCE TO RELATED APPLICATION

The instant application claims priority to Malaysian Patent Application No. PI 20085032, filed Dec. 12, 2008, pending, and PCT International Application No. PCT/MY2009/000044, filed on Feb. 27, 2009, pending, the entire specifications of both of which are expressly incorporated herein by reference.

FIELD OF INVENTION

The present invention relates to a recombinant antigen for the detection of toxocariasis. In more particular, the present invention provides a vector having polynucleotide from TES gene and the polypeptide of recombinant TES antigen which is derived from *Toxocara* larvae cultured in vitro. It also provides a method for detecting toxocariasis using the recombinant TES antigen.

BACKGROUND OF THE INVENTION

Toxocariasis is a helminth infection of human which is caused by roundworm, *Toxocara canis* or *Toxocara cati*. This infection occurs when embryonated eggs containing fully developed infective larvae of the *Toxocara* spp. are ingested. The larvae in the human intestine will penetrate the bowel wall and migrate through blood vessels to reach liver, muscles and lungs, even into eye and brain. Therefore, a method for diagnosis and detection of toxocariasis is crucial for its prevention and treatment.

There are hardly any patented technologies relating to the detection or diagnosis of toxocariasis in the prior arts. Most of the serological and immunological studies of nematode parasites disclosed in the prior arts are designed for the diagnosis of heartworm, such as *Dirofilaria immitis* as described in U.S. Pat. No. 6,103,484.

Some patented technologies aim to detect and raise antibodies against various species of nematode parasites, including the species of the genera *Trichinella, Osteragia, Dirofilaria, Toxocara* and others. In U.S. Pat. No. 5,948,644, an isolated polynucleotide segment comprising a nucleotide sequence encoding an excretory-secretory protein having molecular weight of 11 kDa, 17 kDa, 30 kDa, 37 kDa and 81 kDa is disclosed. Apart from that, a purified antigen derived from a parasitic nematode species having molecular weight of 40 kDa is also disclosed in U.S. Pat. No. 5,871,738. These inventions helps to provide antibodies against the antigens and related molecules, and antibody compositions comprising the antibodies, vaccines comprising the antigens and others. However, these methods are complicated and the proteins used are not specific.

Most of the patented technologies use proteins of higher molecular weight in the detection of nematode parasites. In addition, the methods disclosed are not capable of detecting or diagnosing toxocariasis specifically. Even though the excretory-secretory antigens derived from *T. canis* second stage infective larvae (L2) maintained in defined medium in vitro have been extensively used for the immunodiagnosis of human toxocariasis, immunoassays using serum samples from patients with ascariasis, filariasis and strongyloidiasis, however, shows cross-reactivities with the native TES.

Therefore, it is desirable for the present invention to innovate an antigen which is capable of specifically detecting toxocariasis to overcome the drawbacks of the prior arts. As low molecular weight antigens are shown to be more specific than high molecular proteins for detection of toxocariasis, a suitable protein derived from *Toxocara* larvae can be applied to develop a more useful and effective serodiagnostic marker for this disease.

SUMMARY OF INVENTION

The primary object of the present invention is to develop a recombinant protein or antigen which is capable of detecting or diagnosing toxocariasis specifically and effectively.

Another object of the present invention is to provide an antigen having lower molecular weight which is more sensitive and specific for the detection of toxocariasis.

Still another object of the present invention is to provide a vector which expresses a TES polypeptide which can be used as recombinant antigen in the detection of toxocariasis in a biological sample.

Yet another object of the present invention is to develop a specific, sensitive and reliable method to detect and diagnose the presence of antibody against *Toxocara* spp. in a biological sample.

At least one of the preceding objects is met, in whole or in part, by the present invention, in which one of the embodiments of the present invention describes a vector comprising a polynucleotide sequence encoding a polypeptide having an amino acid sequence of SEQ ID NO: 2 for detecting antibody against *Toxocara* spp. in a biological sample. Preferably, the vector is a gluthathione-S-transferase (GST)-tagged vector.

Another embodiment of the present invention is a bacterial cell comprising a vector which expresses a polypeptide having an amino acid sequence of SEQ ID NO: 2 for detecting antibody against *Toxocara* spp. in a biological sample.

Still another embodiment of the present invention is an isolated polypeptide having an amino acid sequence of SEQ ID NO: 2 for detecting antibody against *Toxocara* spp. in a biological sample.

According to one of the preferred embodiments of the present invention, the polypeptide is a recombinant protein or antigen.

Yet another embodiment of the present invention is an isolated polypeptide having an amino acid sequence of SEQ ID NO: 1 encoded by a gluthathione-S-transferase-tagged vector and a TES-26 gene.

Further embodiment of the present invention is a method for detecting antibody against *Toxocara* spp. in a biological sample, comprising: a) cloning a polynucleotide sequence or complementary sequence thereof encoding a polypeptide having an amino acid sequence of SEQ ID NO: 2; b) expressing the clone in an expression vector to obtain the polypeptide; and c) developing an immunoassay using the polypeptide to detect antibody against *Toxocara* spp. in a biological sample.

In another preferred embodiment of the present invention, the polynucleotide sequence is derived from an open reading frame (ORF) or complete coding sequences (cds) of TES-26 gene. Preferably, the expression vector is a GST-tagged vector.

One skilled in the art will readily appreciate that the present invention is well adapted to carry out the objects and obtain the ends and advantages mentioned, as well as those inherent therein. The embodiments described herein are not intended as limitations on the scope of the invention.

BRIEF DESCRIPTION OF THE DRAWINGS

For the purpose of facilitating an understanding of the invention, there is illustrated in the accompanying drawing the preferred embodiments from an inspection of which when considered in connection with the following description, the invention, its construction and operation and many of its advantages would be readily understood and appreciated.

FIG. 1 is the amino acid sequence of the vector inserted with the polypeptide for the detection of antibody against *Toxocara* spp in a biological sample.

FIG. 2 is the polypeptide comprising amino acid sequence coded by the ORF or complete cds of the TES-26.

FIG. 3 is the nucleotide sequences of the oligonucleotides used in the reverse transcriptase-polymerase chain reaction (RT-PCR) for detecting and identifying TES-26 gene and the cloning vector as described by one of the preferred embodiments of the present invention.

DETAILED DESCRIPTION OF THE INVENTION

Figure 4:
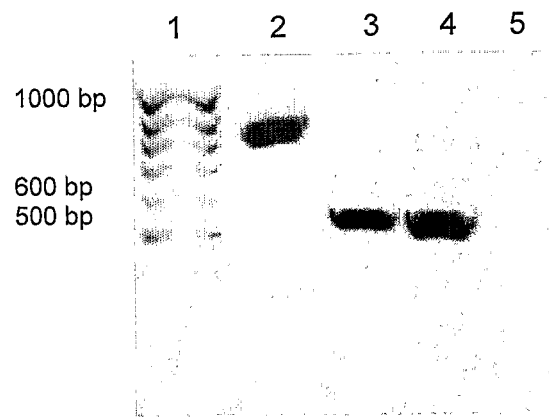
FIG. 4 is the depiction of electrophoresed gel of the amplified RT-PCT products of the TES-26 gene as described by one of the preferred embodiments of the present invention, showing a band size of 793 bp in lane 2. Lane 1 is 100 bp DNA size marker; whereas lane 4 and lane 5, respectively, is the positive and negative control for the RT-PCR reaction.

The present invention relates to a recombinant antigen for the detection of toxocariasis. In more particular, the present invention provides a vector having polynucleotide from TES gene and the polypeptide of recombinant TES antigen which is derived from *Toxocara* larvae cultured in vitro. It also provides a method for detecting toxocariasis using the recombinant TES antigen.

Hereinafter, the invention shall be described according to the preferred embodiments of the present invention and by referring to the accompanying description and drawings. However, it is to be understood that limiting the description to the preferred embodiments of the invention and to the drawings is merely to facilitate discussion of the present invention and it is envisioned that those skilled in the art may devise various modifications without departing from the scope of the appended claim.

The present invention discloses a vector comprising a polynucleotide sequence encoding a polypeptide having an amino acid sequence of SEQ ID NO: 2 for detecting antibody against *Toxocara* spp. in a biological sample.

One of the embodiments of the present invention is an isolated polypeptide having an amino acid sequence of SEQ ID NO: 1 encoded by a gluthathione-S-transferase-tagged vector and a TES-26 gene. FIG. 1 shows the amino acid sequence of the expressed vector with the TES-26 protein, which is denoted as SEQ ID NO: 1. The mino acid sequence of the TES polypeptide is illustrated in FIG. 2. The preferred vector used for the expression of this polypeptide is a GST-tagged vector which is preferably the commercially available PET42™ VERSION "B" (cloning vector).

Preferably, the polynucleotide sequence can be derived from an ORF or complete cds of a TES gene, which is preferably TES-26 gene encoding a 26 kDa protein. The biological sample which can be used for the detection includes human serum, plasma or whole blood (with or without anticoagulant).

Another embodiment of the present invention is a bacterial cell habouring a vector which expresses a polypeptide having an amino acid sequence of SEQ ID NO: 2 for detecting antibody against *Toxocara* spp. in a biological sample. The bacterial cell is an expression host which can be cultured in vitro. According to the preferred embodiment of the present invention, the bacterial host can be BL21(DE3)™ (expression competent cells), XL1-BLUE™ (expression competent cells), DH5α™ (expression competent cells), TOP10™ (expression competent cells) or NOVABLUE™ (expression competent cells) which are commercially available. In the most preferred embodiment, BL21(DE3)™ (expression competent cells) is used as the bacterial host. However, the present invention is not intended to limit the use of suitable hosts available for the expression of the polypeptide.

The present invention also discloses an isolated polypeptide having an amino acid sequence of SEQ ID NO: 2 for detecting antibody against *Toxocara* spp. in a biological sample. This polypeptide is non-glycosylated. Glycosylation of the polypeptide may lead to increase in cross-reactions with antibodies to other organisms that recognize the sugar moieties. Therefore, the non-glycosylated polypeptide invented will not be affected by such cross-reactions. It is also low in molecular weight and suitable to be used for detecting and identifying the presence of antibodies against *Toxocara* spp. in a biological sample sensitively, specifically and reliably.

The recombinant protein, also known as rTES-26, can be used as a sole antigen or in combination with other recombinant antigens such as rTES-30 and/or rTES-120 for detection of human toxocariasis. Besides, this rTES-26 can be employed in immunoassays such as microplate ELISA, dot-blot, Western blot and agglutination assays. It can also be employed in developing rapid tests such as flow-through test and immunochromatography tests (lateral flow test).

Further embodiment of the present invention is a method for detecting antibody against *Toxocara* spp. in a biological sample, comprising: a) cloning a polynucleotide sequence or complementary sequence thereof encoding a polypeptide having an amino acid sequence of SEQ ID NO: 2; b) expressing the clone in an expression vector to obtain the polypeptide; and c) developing an immunoassay using the polypeptide to detect antibody against *Toxocara* spp. in a biological sample.

As set forth in the foregoing description, the polynucleotide sequence applied is derived from an ORF or complete cds of a TES gene, which is preferably the TES-26. Illustrated in FIG. 2 is the polypeptide used in the present method. This polypeptide is coded by the TES-26 gene which comprises amino acid sequence of SEQ ID NO: 2.

The preferred embodiment of the present invention discloses a set of primers comprising nucleotide sequence of SEQ ID NO: 3 and SEQ ID NO: 4 designed for detecting and identifying TES-26 gene in a biological sample that contains *Toxocara* spp. The forward and reverse primers of SEQ ID NO: 3 and SEQ ID NO: 4 as shown in FIG. 3 are designed by referring to the ORF or complete cds of TES-26 gene obtained from GenBank. A RT-PCR is preferably performed using RNA from the biological sample to obtain the nucleotide fragment of TES-26 gene.

Subsequently, the gene encoding TES-26, which is an A-tailed fresh purified RT-PCR product, is preferably cloned into a cloning vector, which is preferably a TOPO vector. However, the present invention are not intended to limit the use of any other commercially available PCR cloning vectors, such as the PJET1.2™ (cloning vector), PT7BLUE T™ (cloning vector), PCR™ II™ (cloning vector), PGEM[R]-T™ (cloning vector) or PLUG-MULTI TA™ (cloning vector). A suitable TOPO vector which can be commercially obtained is the TOPO TA Cloning vector. The plasmid cloned is then transformed into a competent bacteria cell, which is preferably a commercially obtained *Escherichia coli* host. The orientation of the recombinant plasmid can then be confirmed by PCR screening using both TES gene-specific primers (SEQ ID NO: 3 and SEQ ID NO: 4); and vector-specific M13R primer (SEQ ID NO: 5) with TES gene-specific reverse primer (SEQ ID NO: 4). The primer sequences are shown in FIG. 3. The presence of the engineered gene is preferably confirmed by DNA sequencing.

Base mutations may occur during the cloning process. Therefore, an in vitro PCR-based site directed mutagenesis can be performed to correct the base errors occurred in the TES-26-TOPO vector recombinant plasmid before transformation into the expression host. A commercially obtained base mutation-repairing kit can be applied. As shown in the electrophoresed gel in FIG. 4, the amplified RT-PCR products of the ORF of gene encoding TES-26 (lane 2) shows a band size of approximately 793 bp.

As described in one of the preferred embodiments of the present invention, the recombinant plasmid and expression vector can be digested with restriction enzyme before being subcloned into a GST-tagged vector, for example the PET42™ VERSION "B" (cloning vector). The present invention, however, are not intended to limit the use of other suitable expression vectors available to produce the polypeptide targeted. After verified by DNA sequencing, the plasmid constructed is subjected to a transformation process, in which a bacterial cell or host is applied. As set forth in the foregoing description, the bacterial cell is preferably BL21(DE3)™ (expression competent cells). However, other suitable hosts available can also be applied for the expression of this polypeptide.

The recombinant bacteria can be cultured until mid-log phase and the expression is then induced with isopropyl-β-D-thiogalactopyranoside (IPTG). The culture can be harvested after 3 hours and purified under native condition if the recombinant protein is present in sufficient amounts in an active or soluble form. Affinity purification method can be applied wherein the recombinant bacterial cells are lysed in lysis buffer and purified using GST resin. This GST tag is then cleaved or removed by restriction grade site-specific proteases, such as Factor Xa enzyme.

Figure 5:
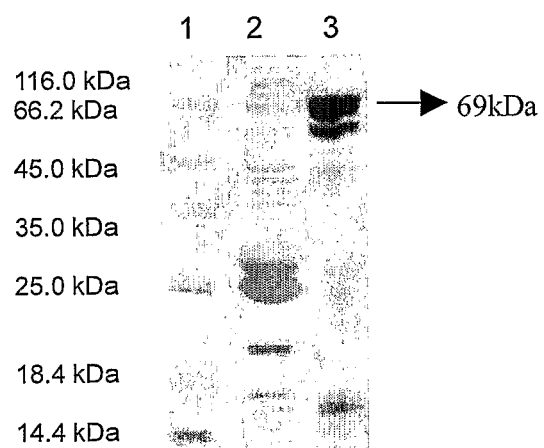
FIG. 5 is the sodium dodecyl sulfate-polyacrylamide gel electrophoresis (SDS-PAGE) profile of the purified TES-26 GST fusion protein of 69 kDa in molecular weight (lane 3). Lane 1 is the protein size marker.

After cleavage of the target protein, Factor Xa is removed by affinity chromatography. The cleavage or removal can be verified by electrophoresis. One of the most preferred methods which can be applied to determined the sizes of protein and polypeptide is the SDS-PAGE. However, the present invention are not intended to limit the use of other suitable methods as well. As shown in FIG. 5, the expressed target protein size determined by SDS-PAGE analysis is of approximately 69 kDa. Since the GST tag is a large molecule of approximately 26 kDa which may affect the immunogenicity of the protein, it was thus necessary to remove the GST tag prior to development of an immunoassay. After cleavage or removal of the GST tag, the molecular weight of the TES-26 recombinant protein shows approximately 30 to 34 kDa.

Figure 6:
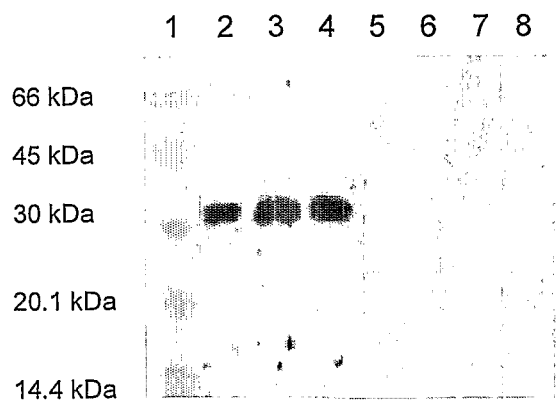
FIG. 6 is the Western blot analysis on recombinant TES-26 antigen probed with various categories of serum. Lane 1 is the protein size marker; lane 2 to 4 refer to three different toxocariasis patients, lane 5 refers to trichuriasis patient; lane 6 refers to toxoplasmosis patient and lane 7 and 8 refer to healthy normals.

Optionally, an analysis of the immunoreactivity of the recombinant protein can be conducted. The preferred method used is Western blot. FIG. 6 shows the Western blot analysis on the recombinant TES-26 antigen probed with various categories of serum, including serum from patients suffering from toxocariasis, trichuriasis, toxoplasmosis and serum from healthy normals. As illustrated in FIG. 6, the antigenicity of the cleaved TES-26 recombinant protein is only reactivity in serum samples from toxocariasis patients. None of the sera from healthy individuals and other helminthic infections show any reactivity.

As set forth in the preceding description, the purified recombinant protein of TES-26 is then used to develop an ELISA test, which is preferably an IgG4-ELISA test for the detection of specific antibody in sera from patients infected with *T. canis*. The preferred procedure is further described in the following examples. Subsequently, the sensitivity and specificity of these assays are evaluated for its usefulness in the detection of toxocariasis using a panel of toxocariasis sera, healthy normals and other helminth related infections. The IgG4-ELISA rTES-26 antigen invented is capable of achieving a sensitivity level of 78% to 85% and specificity level of 95% to 99%.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

EXAMPLE

The invention can be further described with reference to the following examples. These examples are provided to illustrate different aspects and embodiments of the present invention and are not intended in any way to limit the disclosed invention, which is limited only by the claims.

Example 1

PCR Amplification of Coding Sequence of TES-26 Gene

The sequences (open reading frame or complete cds) of TES-26 gene was obtained from Genbank (accession no: U29761). Primers were designed and analyzed with Vector NIT™ version 6.0 (Informac Inc., Invitrogen, USA). The sequences of the forward and reverse primers used are shown in SEQ ID NO: 3 and SEQ ID NO: 4, respectively. RT-PCR was performed by using commercial STRATASCRIPT™ One-Tube RT-PCR System with Easy A™ High-Fidelity PCR Cloning Enzyme kit (Stratagene, USA). The experimental reaction comprised 39.5 μl RNase-free water, 5 μl of 10×RT-PCR buffer, 1 μl of forward and reverse primer (20 pmol/μl each), 1 μl of 40 mM dNTP mix, 1 μl of mRNA sample, 1 μl of diluted STRATASCRIPT™ RT (2.5 U/μl) and 0.5 μl of EASY-A™ HiFi PCR cloning enzyme. All components were added sequentially into 0.2-ml PCR tube to make up a total reaction volume of 50 μl. The amplification process was carried out as follows: first-strand synthesis at 42° C. for 15 minutes; STRATASCRIPT™ RT inactivation at 95° C. for 1 minute; denaturation at 95° C. for 30 sec, template-primer annealing at 60° C. for 30 sec, extension at 68° C. for 2 minutes (40 cycles) and final extension at 68° C. for 5 minutes.

Example 2

Cloning of Genes Encoding TES-26

The A-tailed fresh purified RT-PCR product was cloned into TOPO® TA Cloning vector (PCR2.1 TOPO™ TA—Invitrogen, USA), followed by transformation into TOP10 *E. coli* host Invitrogen, USA). The orientation of the recombinant plasmid was then confirmed by PCR screening using both gene-specific primers (TES26F and TES26R); and vector-specific primer (M13R) and gene-specific primer (TES26R). This is followed by DNA sequencing, and the sequence of the engineered gene was then compared with the published sequences using NIT™ software version 6.0 (Informac Inc., Invitrogen, USA).

Example 3

Repair of Base Mutations

In-vitro PCR-based site directed mutagenesis was performed to correct four base-errors (124, 502, 613 and 768 bp) in TES-26 recombinant plasmid (TES-26/TOPO) using a commercially available kit (QuickChange XL, Stratagene, USA). The amplified RT-PCR products of the ORF of gene encoding TES-26 is shown by gel electrophoresis.

Example 4

Subcloning into Bacterial Expression Vectors

Recombinant plasmid and expression vector were digested with EcoR1 enzyme (Fermentas, USA). After digestion, TES-26 recombinant plasmid was subcloned into PET42™ VERSION "B" (Novagen, Germany) using T4 Rapid DNA Ligation kit (Roche Diagnostics, Germany). After the construct was verified by DNA sequencing, the recombinant plasmid was transformed into an expression host, BL21 (DE3)™ (Novagen, Germany).

Example 5

Expression and Purification of TES-26

The recombinant bacteria was cultured in Terrific broth (TB) containing 30 μg/ml kanamycin and incubated at 37° C. until the $OD_{600}$ reached mid-log phase ($OD_{600}$=0.5). The expression was then induced with isopropyl-β-D-thiogalactopyranoside (IPTG) to a final concentration of 1 mM at 30° C. in an incubator shaker. The culture was then harvested after 3 hours. Subsequently, the recombinant bacterial cells were lysed in lysis buffer containing $NaH_2PO_4$, $KH_2PO_4$, NaCl and KCl by using French press and purified using GST resin (Novagen, Germany). Restriction grade site-specific proteases, Factor Xa enzyme was used for specific cleavage/removal of GST tag using a commercial kit (Factor Xa Cleavage Capture Kit, Novagen, Germany). After cleavage of the target protein, Factor Xa was removed by affinity chromatography using XARREST™ Agarose (Novagen, Germany). The expressed target proteins size were determined by SDS-PAGE analysis.

Example 6

Western Blot

The immunoreactivity of the recombinant protein was analyzed by Western blot technique based on detection IgG4 antibody in serum samples. rTES-26 (20 μg/ml) was electrophoresed in 10% SDS-PAGE and transferred onto nitrocellulose membrane (Osmonic, USA) using a semidry transblot (BioRad, USA). The membrane was cut into strips, blocked with 1% casein blocking solution (Roche Diagnostic, Germany) for 1 hour. Subsequently, the strips were incubated with serum samples (diluted at 1:100 in 0.5% blocking solution) at 4° C., overnight; followed by monoclonal anti-human IgG4-HRP (Zymed, USA) at 1:2000 (in 0.5% blocking solution) for 30 minutes. BM chemiluminescence blotting reagent (Roche Diagnostic, Germany) and X-ray films (Kodak, USA) were used for development of the blots.

Example 7

Enzyme-Linked Immunosorbent Assay (ELISA)

An ELISA based on the rTES-26 antigen was developed and laboratory evaluations were carried out using a panel of sera comprising *Toxocara* infections, other helminth related infections and healthy individuals in order to validate the sensitivity and specificity of the assay. Each well of the 96-well flat-bottomed microtiter plate (NUNC IMMUNO™ Maxisorp, Denmark) was coated with 100 μl of the rTES-26 at an optimum concentration of 10 ug/ml in 0.02 M bicarbonate buffer (pH 9.6). The plate was then covered and incubated in a humid chamber at 4° C., overnight and 37° C. for 2 hours. The plate was washed in phosphate-buffered saline, pH 7.2 containing 0.05% (v/v) Tween-20 (PBS-T), pH 7.2 to remove any unadsorbed antigen. After a washing step of 5×5 minutes, each well was blocked with 1.0% blocking reagent (Roche Diagnostics, Germany) for 1 hour at 37° C. The plate was again washed as previously described, followed by addition of duplicates for each serum dilution (100 μl of human serum diluted at 1:50 in PBS) to each well and incubated at 37° C. for 2 hours. After washing off the excess serum, mouse monoclonal anti-human IgG4-HRP (Zymed, USA) was added at an optimum dilution of 1:1000 (in PBS) and incubated at 37° C. for 30 minutes. Following a final washing step, 2',2-azino-bis [3-ethylbenz-thiazoline-6-sulfonic acid-diammonium salt] (ABTS) substrate (Roche Diagnostics, Germany) was added and the optical densities (O.D) were measured after 30 minutes at absorbance 405 nm (reference 490 nm) using an ELISA spectrophotometer (Tecan, Sweden). An O.D reading of 0.200 was used as the cut-off value (COV) for determination of positivity or to discriminate between positive and negative. This COV was based on mean O.D. reading plus three standard deviations (SD) of 30 serum samples from healthy individuals. The O.D readings were blanked with the PBS (as blank) and O.D readings of equal and/or greater than 0.200 were interpreted as positive cases. The results of sensitivity and specificity evaluations of the IgG4-ELISA are shown in Table 1.

TABLE 1

| Sensitivity evaluation: | | | | |
| --- | --- | --- | --- | --- |
| IgG4-ELISA | Total | Positive | Negative | Sensitivity (%) |
| rTES-26 | 30 | 24 | 6 | 80.0 |

| Specificity evaluation: | |
| --- | --- |
| Types of infection sera | Negative by rTES26-ELISA |
| *A. lumbricoides, T. trichiura*, hookworm | 27/28 (1) |
| *Strongyloides stercoralis* | 4/5 (1) |
| *Gnathostoma spinigerum* | 1/1 (0) |
| *Entamoeba histolytica* | 28/30 (2) |
| *Brugia malayi* (microfilaremic) | 26/28 (2) |
| *Toxoplasma gondii* | 18/20 (2) |
| Healthy individuals | 100/100 (0) |
| Total | 204/212 (8) |
| | Specificity (96.2%) |

The invention claimed is:

1. A method for detection of an antibody against *Toxocara* spp. in a biological sample, comprising:
   cloning a polynucleotide sequence or complementary sequence thereof encoding a non-glycosylated polypeptide having an amino acid sequence of SEQ ID NO: 2 to obtain a recombinant plasmid;
   subcloning the recombinant plasmid in a glutathione-S-transferase-tagged vector;
   transforming the subcloned plasmid in a bacterial host to express the polypeptide; and
   conducting an immunoassay wherein the polypeptide is used as an antigen to detect the antibody against *Toxocara* spp. in the biological sample.

2. A method according to claim 1, wherein the polynucleotide sequence is derived from an open reading frame or complete coding sequences of TES-26 gene.

3. A method according to claim 1 further comprising a step of correcting any base mutation in the recombinant plasmid before the subcloning step.

* * * * *

SEQUENCE LISTING

<160> NUMBER OF SEQ ID NOS: 5

<210> SEQ ID NO 1
<211> LENGTH: 552
<212> TYPE: PRT
<213> ORGANISM: ARTIFICIAL
<220> FEATURE:
<223> OTHER INFORMATION: SYNTHETIC CONSTRUCT

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Glu Tyr Leu Glu Glu Lys Tyr Glu Glu His
            20                  25                  30

Leu Tyr Glu Arg Asp Glu Gly Asp Lys Trp Arg Asn Lys Lys Phe Glu
        35                  40                  45

Leu Gly Leu Glu Phe Pro Asn Leu Pro Tyr Tyr Ile Asp Gly Asp Val
    50                  55                  60

Lys Leu Thr Gln Ser Met Ala Ile Ile Arg Tyr Ile Ala Asp Lys His
65                  70                  75                  80

Asn Met Leu Gly Gly Cys Pro Lys Glu Arg Ala Glu Ile Ser Met Leu
                85                  90                  95

Glu Gly Ala Val Leu Asp Ile Arg Tyr Gly Val Ser Arg Ile Ala Tyr
            100                 105                 110

Ser Lys Asp Phe Glu Thr Leu Lys Val Asp Phe Leu Ser Lys Leu Pro
        115                 120                 125

Glu Met Leu Lys Met Phe Glu Asp Arg Leu Cys His Lys Thr Tyr Leu
    130                 135                 140

Asn Gly Asp His Val Thr His Pro Asp Phe Met Leu Tyr Asp Ala Leu
145                 150                 155                 160

Asp Val Val Leu Tyr Met Asp Pro Met Cys Leu Asp Ala Phe Pro Lys
                165                 170                 175

Leu Val Cys Phe Lys Lys Arg Ile Glu Ala Ile Pro Gln Ile Asp Lys
            180                 185                 190

Tyr Leu Lys Ser Ser Lys Tyr Ile Ala Trp Pro Leu Gln Gly Trp Gln
        195                 200                 205

Ala Thr Phe Gly Gly Gly Asp His Pro Pro Lys Ser Asp Gly Ser Thr
    210                 215                 220

Ser Gly Ser Gly His His His His His His Ser Ala Gly Leu Val Pro
225                 230                 235                 240

Arg Gly Ser Thr Ala Ile Gly Met Lys Glu Thr Ala Ala Ala Lys Phe
                245                 250                 255

Glu Arg Gln His Met Asp Ser Pro Asp Leu Gly Thr Gly Gly Gly Ser
            260                 265                 270

Gly Ile Glu Gly Arg Gly Ser Met Asp Ile Gly Asp Pro Asn Ser Pro
        275                 280                 285

Phe Thr Met Ser Val Val His Lys Ala Cys Leu Ile Ala Leu Leu Phe
    290                 295                 300

Val Ser Ser Gly Val Ala Gln Gln Cys Met Asp Ser Ala Ser Asp Cys
305                 310                 315                 320

Ala Ala Asn Ala Gly Ser Cys Phe Thr Arg Pro Val Ser Gln Val Leu
                325                 330                 335

Gln Asn Arg Cys Gln Arg Thr Cys Asn Thr Cys Asp Cys Arg Asp Glu
            340                 345                 350

```
Ala Asn Asn Cys Ala Ala Ser Ile Asn Leu Cys Gln Asn Pro Thr Phe
            355                 360                 365

Glu Pro Leu Val Arg Asp Arg Cys Gln Lys Thr Cys Gly Leu Cys Ala
370                 375                 380

Gly Cys Gly Phe Ile Ser Ser Gly Ile Val Pro Leu Val Val Thr Ser
385                 390                 395                 400

Ala Pro Ser Arg Arg Val Ser Val Thr Phe Ala Asn Asn Val Gln Val
                405                 410                 415

Asn Cys Gly Asn Thr Leu Thr Thr Ala Gln Val Ala Asn Gln Pro Thr
            420                 425                 430

Val Thr Trp Glu Ala Gln Pro Asn Asp Arg Tyr Thr Leu Ile Met Val
            435                 440                 445

Asp Pro Asp Phe Pro Ser Ala Ala Asn Gly Gln Gln Gly Gln Arg Leu
450                 455                 460

His Trp Trp Val Ile Asn Ile Pro Gly Asn Asn Ile Ala Gly Gly Thr
465                 470                 475                 480

Thr Leu Ala Ala Phe Gln Pro Ser Thr Pro Ala Ala Asn Thr Gly Val
                485                 490                 495

His Arg Tyr Val Phe Leu Val Tyr Arg Gln Pro Ala Ala Ile Asn Ser
            500                 505                 510

Pro Leu Leu Asn Asn Leu Val Val Gln Asp Ser Glu Arg Pro Gly Phe
            515                 520                 525

Gly Thr Thr Ala Phe Ala Thr Gln Phe Asn Leu Gly Ser Pro Tyr Ala
            530                 535                 540

Gly Asn Phe Tyr Arg Ser Gln Ala
545                 550

<210> SEQ ID NO 2
<211> LENGTH: 262
<212> TYPE: PRT
<213> ORGANISM: TOXOCARA CANIS

<400> SEQUENCE: 2

Met Ser Val Val His Lys Ala Cys Leu Ile Ala Leu Leu Phe Val Ser
1               5                   10                  15

Ser Gly Val Ala Gln Gln Cys Met Asp Ser Ala Ser Asp Cys Ala Ala
            20                  25                  30

Asn Ala Gly Ser Cys Phe Thr Arg Pro Val Ser Gln Val Leu Gln Asn
            35                  40                  45

Arg Cys Gln Arg Thr Cys Asn Thr Cys Asp Cys Arg Asp Glu Ala Asn
50                  55                  60

Asn Cys Ala Ala Ser Ile Asn Leu Cys Gln Asn Pro Thr Phe Glu Pro
65                  70                  75                  80

Leu Val Arg Asp Arg Cys Gln Lys Thr Cys Gly Leu Cys Ala Gly Cys
                85                  90                  95

Gly Phe Ile Ser Ser Gly Ile Val Pro Leu Val Val Thr Ser Ala Pro
            100                 105                 110

Ser Arg Arg Val Ser Val Thr Phe Ala Asn Asn Val Gln Val Asn Cys
            115                 120                 125

Gly Asn Thr Leu Thr Thr Ala Gln Val Ala Asn Gln Pro Thr Val Thr
130                 135                 140

Trp Glu Ala Gln Pro Asn Asp Arg Tyr Thr Leu Ile Met Val Asp Pro
145                 150                 155                 160

Asp Phe Pro Ser Ala Ala Asn Gly Gln Gln Gly Gln Arg Leu His Trp
                165                 170                 175
```

```
Trp Val Ile Asn Ile Pro Gly Asn Asn Ile Ala Gly Gly Thr Thr Leu
            180                 185                 190

Ala Ala Phe Gln Pro Ser Thr Pro Ala Ala Asn Thr Gly Val His Arg
            195                 200                 205

Tyr Val Phe Leu Val Tyr Arg Gln Pro Ala Ala Ile Asn Ser Pro Leu
    210                 215                 220

Leu Asn Asn Leu Val Val Gln Asp Ser Glu Arg Pro Gly Phe Gly Thr
225                 230                 235                 240

Thr Ala Phe Ala Thr Gln Phe Asn Leu Gly Ser Pro Tyr Ala Gly Asn
                245                 250                 255

Phe Tyr Arg Ser Gln Ala
            260

<210> SEQ ID NO 3
<211> LENGTH: 28
<212> TYPE: DNA
<213> ORGANISM: ARTIFICIAL
<220> FEATURE:
<223> OTHER INFORMATION: PRIMER

<400> SEQUENCE: 3
caccatgtca gttgtacaca aagcttgc                                        28

<210> SEQ ID NO 4
<211> LENGTH: 20
<212> TYPE: DNA
<213> ORGANISM: TOXOCARA CANIS

<400> SEQUENCE: 4
ttaggcctgc gatcgataga                                                 20

<210> SEQ ID NO 5
<211> LENGTH: 17
<212> TYPE: DNA
<213> ORGANISM: ARTIFICIAL
<220> FEATURE:
<223> OTHER INFORMATION: PRIMER

<400> SEQUENCE: 5
caggaaacag ctatgac                                                    17
```